(12) United States Patent
De Kort et al.

(10) Patent No.: US 8,445,450 B2
(45) Date of Patent: *May 21, 2013

(54) ANTITHROMBOTIC DUAL INHIBITORS COMPRISING A BIOTIN RESIDUE

(75) Inventors: Martin De Kort, Oss (NL); Constant Adriaan Anton Van Boeckel, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,905

(22) Filed: Apr. 4, 2012

(65) Prior Publication Data

US 2012/0245109 A1    Sep. 27, 2012

Related U.S. Application Data

(62) Division of application No. 11/722,444, filed as application No. PCT/EP2005/057011 on Dec. 21, 2005, now Pat. No. 8,168,595.

(30) Foreign Application Priority Data

Dec. 23, 2004    (EP) .................................... 04106964

(51) Int. Cl.
*A61K 31/7052*    (2006.01)
*C07H 15/20*    (2006.01)

(52) U.S. Cl.
USPC ............................ 514/25; 536/17.3; 536/18.1

(58) Field of Classification Search
USPC .................... 514/25; 536/17.3, 18.1
See application file for complete search history.

(56) References Cited

U.S. PATENT DOCUMENTS

| 6,486,129 | B1 * | 11/2002 | Tromp et al. | 514/32 |
| 8,168,595 | B2 * | 5/2012 | De Kort et al. | 514/25 |
| 8,183,228 | B2 * | 5/2012 | De Kort et al. | 514/54 |

FOREIGN PATENT DOCUMENTS

WO    WO 02/24754    *    3/2002

OTHER PUBLICATIONS

Sundaram et al, Proceedings of the National Academy of Sciences, 2003, 100(2), 651-56.*
The Merck Index, 1996, pp. 151-152.*
Wilbur et al, Bioconjugate Chem. 2001, 12, 616-23.*

* cited by examiner

*Primary Examiner* — Shaojia Anna Jiang
*Assistant Examiner* — Ganapathy Krishnan
(74) *Attorney, Agent, or Firm* — Richard S. Parr; Catherine D. Fitch

(57) ABSTRACT

The present invention relates compounds of the formula (I)

$$\text{oligosaccharide-spacer-A} \qquad (I),$$

Figure 1:
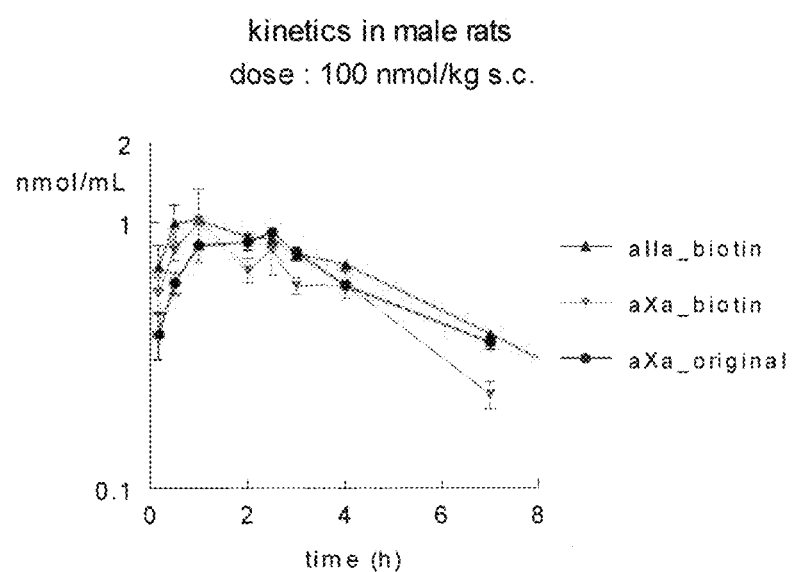

wherein the oligosaccharide is a negatively charged oligosaccharide residue comprising two to twenty five monosaccharide units, the charge being compensated by positively charged counterions, and wherein the oligosaccharide residue is derived from an oligosaccharide which has (AT-III mediated) anti-Xa activity per se;
the spacer is an essentially pharmacologically inactive flexible linking residue having a chain length of 10 to 70 atoms;
A is the residue —CH[NH—SO$_2$—R$^1$][CO—NR$^2$—CH(4-benzamidine)-CO—NR$^3$R$^4$].

9 Claims, 2 Drawing Sheets

ANTITHROMBOTIC DUAL INHIBITORS COMPRISING A BIOTIN RESIDUE

The present invention relates to new antithrombotic dual inhibitors comprising a biotin residue or a biotin derivative, a process for their preparation, pharmaceutical compositions containing the compounds as active ingredients, as well as the use of said compounds for the manufacture of medicaments.

Recent progress in the search for synthetic active pharmaceutical substances having similar or superior antithrombotic properties when compared to heparin, has resulted in the design of new dual inhibitors e.g. as described in WO 99/65934 and WO 01/42262. Those compounds are typically conjugates of an oligosaccharide residue connected to a direct thrombin inhibitor by an essentially pharmacologically inactive spacer. The oligosaccharide residue in the molecule displays anti-thrombin III (AT-III) mediated anti-Xa activity. Thus, the new conjugates have dual, antithrombotic and anticoagulant, activity.

An excellent example of the new class of dual inhibitors is the compound indicated with the code name Org 42675, in which a pentasaccharide is linked to a direct inhibitor of thrombin, having the following structure:

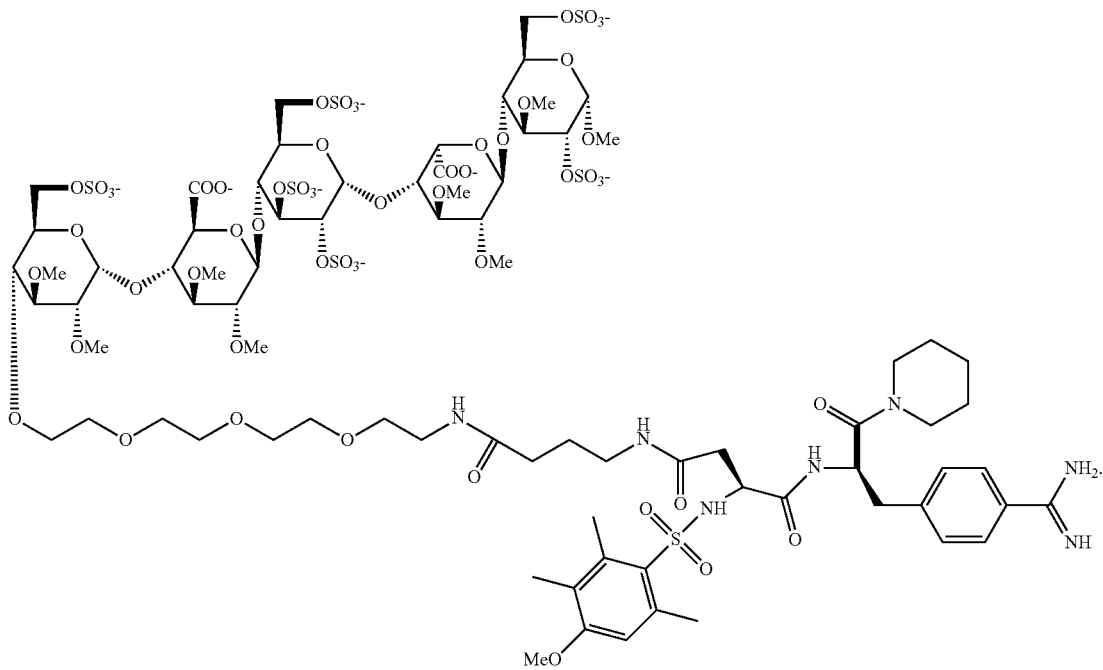

Studies in experimental thrombosis have demonstrated that this compound, in addition to potent anticoagulant and antithrombotic properties, also inhibits the activity of clot-bound thrombin. Further, Org 42675 appeared to be highly efficacious in the prevention of thrombotic reocclusion following thrombolysis of occlusive arterial thrombi. The compound displays a 10-fold prolonged half-life in comparison to the corresponding non-conjugated direct thrombin inhibitor derived from NAPAP. In comparison with argatroban, heparin and fondaparinux, Org 42675 showed improved efficacy. (Journal of Thrombosis and Haemostasis, Volume 1, Issue 9, Page 1945, 2003).

The clinical potential of the new dual inhibitors is considered to be significant and therefore clinical testing has already been initiated.

As a precautionary measure, within the field of anticoagulant and antithrombotic therapy, there is a need for an antidote to be able to effectively neutralize or minimize the activity of the anticoagulant or antithrombotic drug used. This is because it is well known that a hemorrhage can be triggered in a patient under treatment for any accidental cause. Further, it may be necessary to intervene surgically in a patient under antithrombotic or anticoagulant treatment. In addition, during some surgical procedures, anticoagulants may be used at a high dose so as to prevent blood coagulation and it is necessary to neutralize them at the end of the operation. It is therefore advantageous to have antithrombotic/anticoagulant agents available which can be neutralized in order to stop the antithrombotic/anticoagulant activity at any time.

In US 2004/0024197 it is disclosed that, in case of emergency, the antithrombotic activity of certain polysaccharides may be reduced using avidin, if those polysaccharides contain at least a covalent bond with biotin or a biotin derivative.

The present invention relates to novel neutralizable dual inhibitors derived from the dual inhibitors described in WO 99/65934 and WO 01/42262. It has been found that a certain biotin "label", being the group

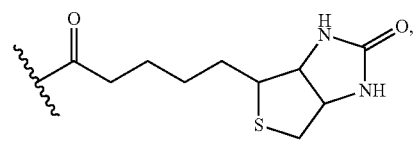 [SMILES: *C(=O)CCCCC1SCC2NC(=O)NC21]

also referred to in this document as "BT" (derived from hexahydro-2-oxo-1H-thieno[3,4-d]imidazole-4-pentanoic acid, preferably the D(+)-isomer) or an analogue thereof, can be attached to or introduced into the structure of the compounds described in WO 99/65934 and WO 01/42262, resulting in neutralizable dual inhibitors.

Thus, the present invention relates to compounds of the formula (I)

oligosaccharide-spacer-A (I), wherein the oligosaccharide is a negatively charged oligosaccharide residue comprising two to twenty five monosaccharide units, the charge being compensated by positively charged counterions, and wherein the oligosaccharide residue is derived from an oligosaccharide which has (AT-III mediated) anti-Xa activity per se;

the spacer is an essentially pharmacologically inactive flexible linking residue having a chain length of 10 to 70 atoms;

A is the residue —CH[NH—SO$_2$—R$^1$][CO—NR$^2$—CH(4-benzamidine)-CO—NR$^3$R$^4$], wherein R$^1$ is phenyl, naphthyl, 1,2,3,4-tetrahydronaphthyl, (iso)quinolinyl, tetrahydro(iso)quinolinyl, 3,4-dihydro-1H-isoquinolinyl, chromanyl or the camphor group, which groups may optionally be substituted with one or more substituents selected from (1-8C)alkyl or (1-8C)alkoxy; and wherein R$^2$ and R$^3$ are independently H or (1-8C)alkyl; R$^4$ is (1-8C)alkyl or (3-8C)cycloalkyl; or R$^3$ and R$^4$ together with the nitrogen atom to which they are bonded are a nonaromatic (4-8) membered ring optionally containing another heteroatom, the ring optionally being substituted with (1-8C)alkyl or SO$_2$-(1-8C)alkyl;

or a pharmaceutically acceptable salt thereof or a prodrug or solvate thereof;

wherein the compound of formula I further comprises at least one covalent bond with a biotin residue or an analogue thereof.

The compounds of the invention are dual inhibitors, having a tuneable mixed profile of both non-mediated, direct anti-thrombin (factor IIa) activity and anti-thrombin III (AT-III) mediated anti-Xa activity. The mixed profile of the compounds of the invention may be tuned by varying the nature of the oligosaccharide residue and the potency of the direct thrombin inhibitor (NAPAP analogues). A range of profiles is thereby available. Compounds of the invention have a long plasma half-life and, as a result, they possess prolonged anti-thrombin activity compared to NAPAP or its derivatives reported in literature previously. In addition, compounds of the invention may escape the neutralizing action of platelet factor 4 (PF4). Low toxicity is also an advantageous aspect of compounds of this invention.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

The biotin label (or analogue thereof) in the compound of the present invention is rapidly recognized by and binds to a specific antidote, being avidin (The Merck Index, Twelfth edition, 1996, M.N. 920, pages 151-152) or streptavidin, two tetrameric proteins with respective masses equal to approximately 66 000 and 60 000 Da which have a very high affinity for biotin. Thus, in an emergency situation, the action of the dual inhibitor can be rapidly neutralized by using avidin or streptavadin, for example by injection of a pharmaceutical solution containing the same. Analogues of avidin and streptavidin having high biotin affinity may be used similarly. The resulting inactive antidote-inhibitor complex is cleared from the blood circulation.

Biotin analogues, which may be used as a label according to this invention, may be selected from, but are not limited to, the biotin analogues shown in the Pierce catalogue, 1999-2000, pages 62 to 81, for example 6-biotinamidohexanoate, 6-(6-biotinamidohexanamido)hexanoate, and 2-biotinamidoethanethiol, etc. In such analogues, the biotin residue BT, as previously defined, is a characteristic part of the molecule. Other analogues are for example biotin analogues that are alkyated at the biotinamide bond (wherein alkyl is (1-4C) alkyl, preferably methyl) and which are stable to biotinidase cleavage (*Bioconjugate Chem.*, Vol. 11, 2000, 569-583; *Bioconjugate Chem.*, Vol. 11, 2000, 584-598) or other biotin analogues comprising for example a hydroxymethylene, carboxylate, or acetate alpha to the biotinamide bond, such as described in *Bioconjugate Chem.*, Vol. 12, No. 4, 2001, 616-623.

Preferred residues of biotin analogues have the formula —(NH—CO)$_n$—(CH$_2$)$_p$—NR—BT, wherein n is 0 or 1 (in particular n is 0), p is 4 or 5 (in particular p is 4), R=H or (1-4C)alkyl and BT is as previously defined. In preferred embodiments, R is H.

It has been found in comparative studies with their corresponding non-biotinylated compounds that the introduction of a biotin label into the dual inhibitors of this invention does essentially not interfere with their direct thrombin inhibitory potency nor with their anti-thrombin III (AT-III) mediated anti-Xa activity. In addition, the antithrombotic activity of the compounds of formula I is (essentially) completely neutralized upon administration of avidin or streptavidin.

Any negatively charged oligosaccharide residue of two to twenty five monosaccharide units is usable in the compounds of the present invention. Suitable compounds of the invention are compounds wherein the oligosaccharide is a sulfated oligosaccharide residue. Preferably, the oligosaccharide residue is derived from an oligosaccharide which has (AT-III mediated) anti-Xa activity per se, such as the oligosaccharides disclosed in EP 0,454,220, EP 0,529,715, WO 97/47659, WO 98/03554, WO 99/36443 and WO 99/36428. Further preferred are oligosaccharide residues having two to sixteen, in particular two to six, monosaccharide units. Most preferably the oligosaccharide is a sulfated pentasaccharide residue. Preferred pentasaccharide residues have the formula (II)

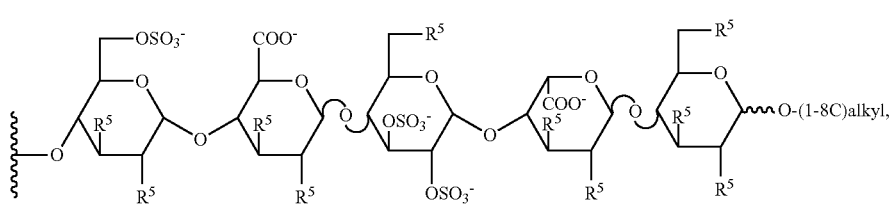

(II)

wherein $R^5$ is independently a biotin residue or analogue thereof, $OSO_3^-$ or (1-8C)alkoxy. In preferred pentasaccharide residues, the total number of sulfate groups is 4, 5, 6 or 7.

Preferred compounds according to the invention are compounds wherein the pentasaccharide residue has the structure:

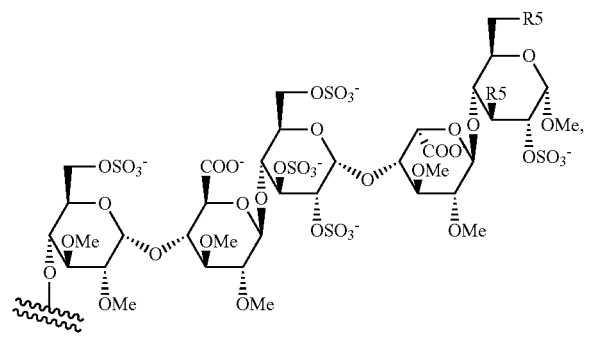

wherein $R^5$ is $OCH_3$ or $OSO_3^-$.

An in particular preferred pentasaccharide residue is

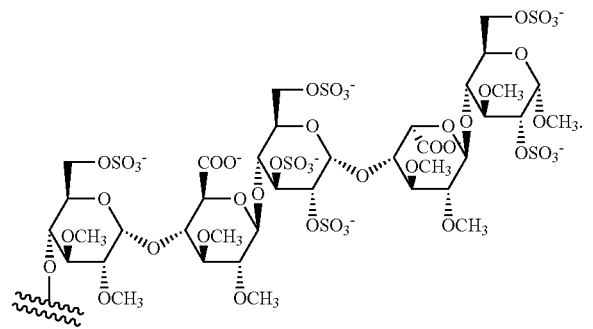

Further preferred compounds of the invention are compounds of formula I, wherein $R^1$ is phenyl or naphthyl, optionally substituted with one or more substituents selected from methyl or methoxy. More preferred, $R^1$ is 4-methoxy-2,3,6-trimethylphenyl. In preferred compounds, $NR^3R^4$ represents the piperidinyl group. Preferably, $R^2$ is H.

The spacer is an essentially pharmacologically inactive flexible linking residue, preferably having 10-50 atoms counted along the "backbone" of the spacer, the oxygen of the oligosaccharide residue not included. Further preferred is a length of 13-25 atoms, preferably 16-22, and most preferred 19 atoms.

The chemical nature of the spacer is of minor importance for the anti-thrombotic activity of the compounds of the invention. The spacer may comprise (somewhat) rigid elements, such as ring structures and unsaturated bonds. Highly flexible spacers are more suitable than others. Suitable spacers may easily be designed by a person skilled in the art. For synthetic reasons longer spacers are considered less suitable, however, longer spacers may still succesfully be applied in the compounds of the present invention. Preferred spacers comprise at least one —$(CH_2CH_2O)$— element.

Preferred compounds according to the invention comprise one covalent bond with a biotin residue or analogue thereof.

The biotin (or analogue thereof) label may be present in all parts of the compound formula I. Therefore, embodiments of this invention are compounds wherein (a) the oligosaccharide residue of the compound of formula I comprises a covalent bond with a biotin residue or analogue thereof, (b) the spacer of the compound of formula I comprises a covalent bond with a biotin residue or analogue thereof and (c) the residue A of the compound of formula I comprises a covalent bond with a biotin residue or analogue thereof (which means that a hydrogen atom or substituent in the definition of A has been replaced by the biotin residue).

Representative examples of the biotinylated dual inhibitors of the present invention are (III)

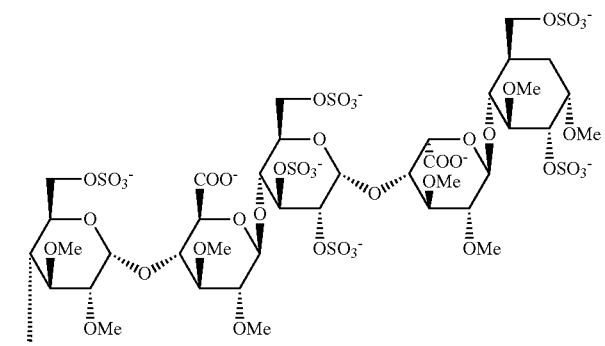

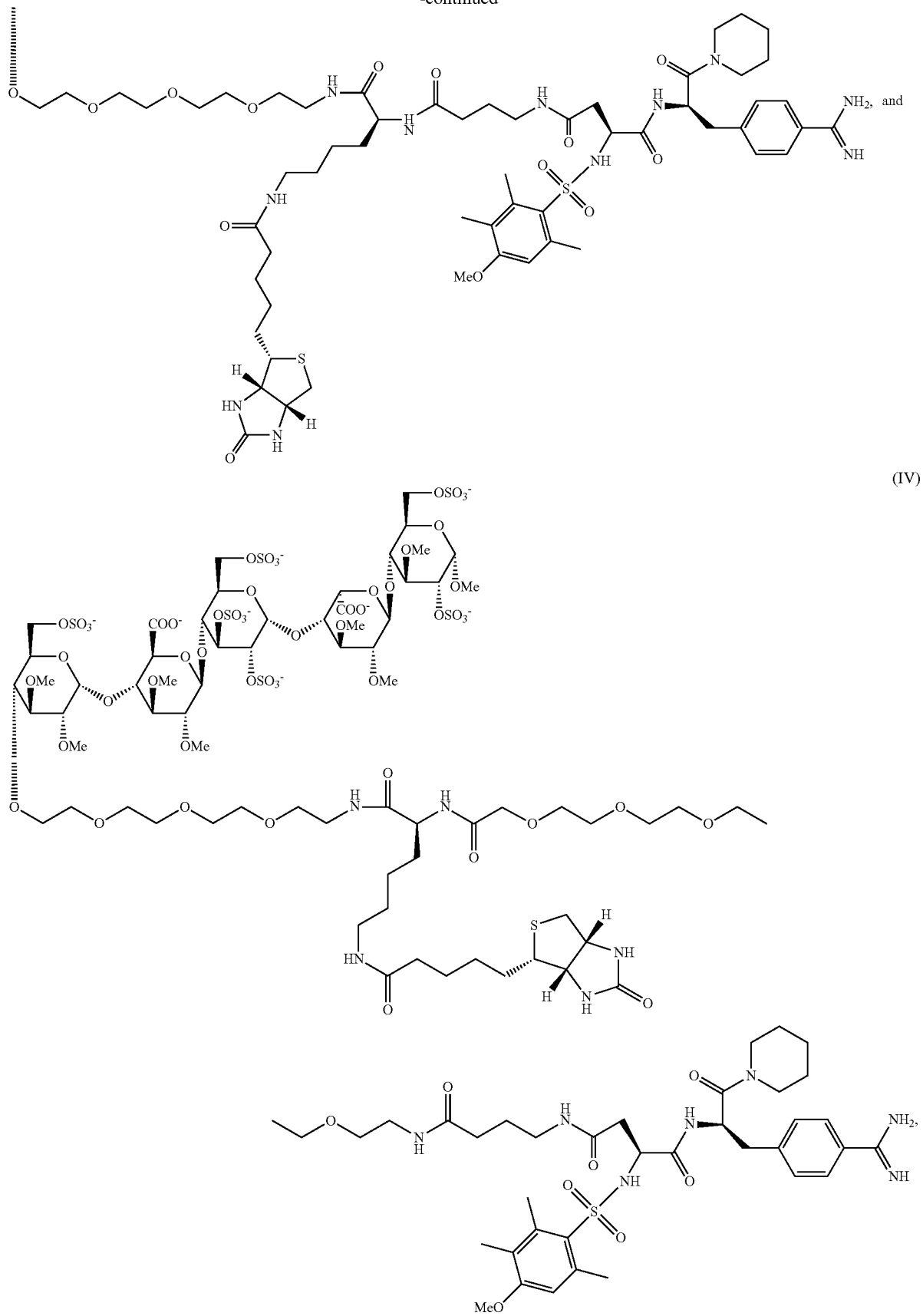

and salts thereof, but also compounds of formula I, wherein the spacer is attached to the oligosaccharide at another position, and/or compounds wherein the biotin (analogue) residue is present at other positions of the molecule. Preferred is the sodium salt.

The compound of formula III is a preferred example of this invention.

In the description of the compounds of formula (I) the following definitions are used.

The terms (1-4C)alkyl and (1-8C)alkyl mean a branched or unbranched alkyl group having 1-4 and 1-8 carbon atoms, respectively, for example methyl, ethyl, propyl, isopropyl, butyl, sec-butyl, tert-butyl, hexyl and octyl. Methyl and ethyl are preferred alkyl groups.

The term (1-8C)alkoxy means an alkoxy group having 1-8 carbon atoms, the alkyl moiety having the meaning as previously defined. Methoxy is a preferred alkoxy group.

The term (3-8C)cycloalkyl means a cycloalkyl group having 3-8 carbon atoms, being cyclopropyl, cyclobutyl, cyclopentyl, cyclohexyl, cycloheptyl or cyclo-octyl. Cyclopentyl and cyclohexyl are preferred cycloalkyl groups.

The spacer length is the number of atoms of the spacer, counted along the shortest chain between the oligosaccharide residue and the peptide part of the molecule, not counting the oxygen atom of the oligosaccharide residue which is connected to the spacer.

The term "prodrug" means a compound of the invention in which for instance the amino group of the amidino-moiety is protected, e.g. by hydroxy or a (1-6C)alkoxycarbonyl group.

Solvates according to the invention include hydrates.

With regard to the synthetic way in which the biotin residue is attached to compounds of the formula I the chemical literature offers several possibilities which can be utilized and by which different sets of protective groups well known to a person skilled in the art can be employed.

The biotin residue, comprising a reactive group of for instance the activated ester, maleimide, iodoacetyl or primary amine type, will preferably be reacted with an amine functional group, or a thiol functional group, or a carboxylic acid functional group, or an aldehyde functional group, the reaction taking place according to the conditions described in the literature (cf. Savage et al., Avidin-Biotin Chemistry: A Handbook; Pierce Chemical Company, 1992).

The biotin residue can for instance be bonded directly to the (negatively charged) oligosaccharide residue or via an optionally N-(1-4C)alkylated amino functional group of a oligosaccharide-spacer residue or via an optionally N-(1-4C) alkylated amino acid residue to an optionally N-(1-4C)alkylated amine functional group of the oligosaccharide residue of the compound of formula I.

In another aspect of this invention the biotin residue can for instance be bonded directly to residue A or via an optionally N-(1-4C)alkylated amino functional group of a linking residue or via an optionally N-(1-4C)alkylated amino acid residue to an optionally N-(1-4C)alkylated amine functional group of residue A of the compound of formula I.

Yet in another aspect of this invention the biotin residue can for instance be introduced stepwise by first bonding directly to residue A or via an optionally N-(1-4C)alkylated amino functional group of a part of the spacer of formula I or via an optionally N-(1-4C)alkylated amino acid residue to an optionally N-(1-4C)alkylated amine functional group of residue A of the compound of formula I and second bonding directly to an oligosaccharide or via an optionally N-(1-4C) alkylated amino functional group of part of the spacer of formula I or via an optionally N-(1-4C)alkylated amino acid residue to an optionally N-(1-4C)alkylated amine functional group of the (negatively charged) oligosaccharide of the compound of formula I, or vice versa. In another aspect of the invention optionally N-alkylated amino acid residues or α-N-substituted (beta-)amino acid analogues such as described in [*Bioconjugate Chem.*, Vol. 12, No. 4, 2001, 616-623] may be introduced by a peptide coupling using methods known in the art. The azido group is a suitable latent amine functional group which can be used in precursors of the compound of the formula I for the subsequent introduction of the biotin residue.

A preferred process for the preparation of the compound of formula I comprises a step wherein the benzamidine moiety in the residue A is in the form of a precursor, preferably being the 1,2,4-oxadiazolin-5-one group, and is subsequently converted into the benzamidine by deprotection, in particular by hydrogenation (Bolton, R. E. et al, Tetrahedron Letters, Vol 36, No 25, 1995, pp 4471-4474).

The compounds of the present invention are further prepared by derivatizing NAPAP (or a NAPAP-analogue) at the glycine position with cysteine or lysine or aspartate using methods generally known in the art, which compound subsequently (a) is coupled to a oligosaccharide-spacer residue or (b) is coupled to a spacer, which then is derivatized with a thiol functional group or a carboxylic acid functional group and subsequently is coupled to an oligosaccharide residue. Any suitable oligosaccharide may be used for this purpose, for example oligosaccharides known in literature (e.g. from EP 0,454,220 and EP 0,529,715, but not limited to these sources) or commercially available oligosaccharides. The coupling of the spacer to the oligosaccharide can for instance be performed by using the methods described in EP 0,649, 854.

The peptide coupling, a procedural step in the above described method to prepare the compounds of the invention, can be carried out by methods commonly known in the art for the coupling—or condensation—of peptide fragments such as by the azide method, mixed anhydride method, activated ester method, the carbodiimide method, or, preferably, under the influence of ammonium/uronium salts like TBTU, especially with the addition of catalytic and racemisation suppressing compounds like N-hydroxysuccinimide, N-hydroxybenzotriazole and 7-aza-N-hydroxybenzotriazole. Overviews are given in *The Peptides, Analysis. Synthesis. Biology*, Vol 3, E. Gross and J. Meienhofer, eds. (Academic Press, New York, 1981) and *Peptides: Chemistry and Biology*, N. Sewald and H.-D. Jakubke (Wiley-VCH, Weinheim, 2002).

Amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, the 9-fluorenylmethyloxycarbonyl (Fmoc) group or the phthaloyl (Phth) group, or may be introduced by demasking of an azide moiety. Overviews of amino protecting groups and methods for their removal is given in the above mentioned *The Peptides. Analysis, Synthesis, Biology*, Vol 3 and *Peptides: Chemistry and Biology*.

The compounds of the invention, which can occur in the form of a free base, may be isolated from the reaction mixture in the form of a pharmaceutically acceptable salt. The pharmaceutically acceptable salts may also be obtained by treating the free base of formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention or intermediates thereof possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally. The exact dose and regimen of these compounds and compositions thereof will neccessarily be dependent upon the needs of the individual subject to whom the medicament is being administered, the degree of affliction or need and the judgment of the medical practitioner. In general, parenteral administration requires lower dosages than other methods of administration which are more dependent upon absorption. However, the daily dosages are for humans preferably 0.001-100 mg per kg body weight, more preferably 0.01-10 mg per kg body weight.

The medicament manufactured with the compounds of this invention may also be used as adjuvant in acute anticoagulant therapy. In such a case, the medicament is administered with other compounds useful in treating such disease states.

Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

LEGENDS TO FIGURES

FIG. 1. Mean plasma levels determined by measurement of the anti-Xa or anti-IIa activity after s.c. administration of 100 nmol/kg of the biotinylated compound III of this invention ("biotin"). Besides the plasma levels are given of Org 42675 ("original") after determination of the anti-Xa activity.

Figure 2:
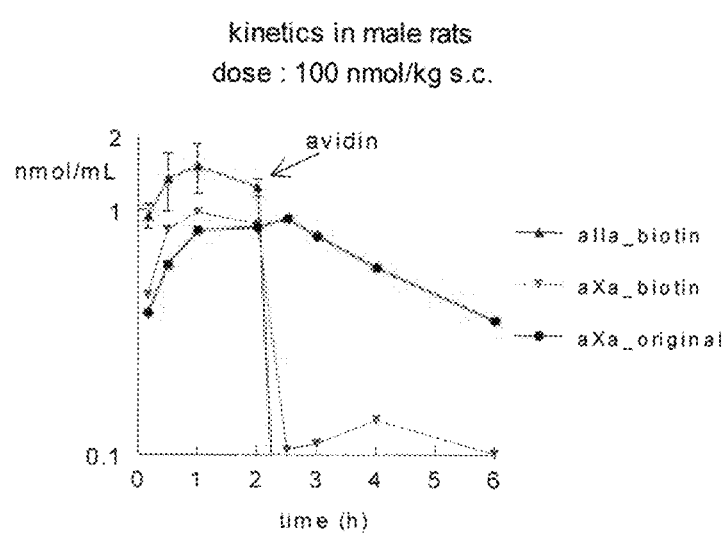

FIG. 2. Shows the mean plasma levels±s.e.m. after s.c. administration of 100 nmol/kg compound. At t=2 h avidin (10 mg/kg) was administered i.v. to those rats treated with compound III of this invention ("biotin") or Org 42675 ("original"). The pharmacokinetic behavior of compound III of this invention is effected by administration of Avidin in contrast to the behavior of the original compound.

The invention is further illustrated by the following examples.

EXAMPLES

Abbreviations Used

Aq.=aqueous
ATM=antithrombin III
Boc=tert-butyloxycarbonyl
DCM=dichloromethane
DiPEA=N,N-diisopropylethylamine
DMF=N,N-dimethylformamide
Et=ethyl
fmoc=9-fluorenylmethoxycarbonyl
NMM=N-methyl morpholine
Me=methyl
sat.=saturated
PRP=platelet rich plasma
PPP=platelet poor plasma
RT=room temperature
TBTU=2-(1H-benzotriazol-1-yl)-1,1,3,3-tetramethyluronium tetrafluoroborate
TFA=trifluoroacetic acid
THF=tetrahydrofuran

Example 1

Scheme 1

$N^\epsilon$-(D-(+)-biotinyl)-N-{4-[[4-[[(1R)-1-[[4-(1,2,4-oxadiazol-5-onyl)phenyl]methyl]-2-oxo-2-(1-piperidinyl)ethyl]amino]-3-[[(4-methoxy-2,3,6-trimethylphenyl)sulfonyl]amino]-1,4-(S)-dioxo-butyl]amino]-butanoyl}-L-lysine (3)

Compound 2 (0.20 g, 0.27 mmol), which was prepared as described in WO 01/42262, was dissolved in DCM (10 mL). DiPEA (0.14 mL, 0.81 mmol) was added followed by TBTU (86 mg, 0.27 mmol). After 1 h stirring under an atmosphere of nitrogen, compound 1 ($N^\epsilon$-fmoc-Lys-OH, 0.27 mmol, Fluka) was added as a solid. DMF (5 mL) was added to dissolve the ($N^\epsilon$-fmoc-Lys-OH. The mixture was stirred for 16 h and was poured in a 0.5 N HCl-solution. The solution was extracted with DCM (3×). The combined organic layers were washed with brine, dried (MgSO$_4$) and concentrated under reduced pressure (850 mbar, 45° C.). The crude product was purified by silica column chromatography (DCM/MeOH/AcOH, 99/0/1→89/10/1, v/v/v), Remaining AcOH was removed by repeated concentration in toluene. Further purification was accomplished by HPLC chromatography (ACN/H$_2$O/0.1N TFA, 20:78:3→95:2:3) to give 0.15 g (53%) of the pure compound. TLC: Rf 0.5 (DCM/MeOH/AcOH, 90/9/1, v/v/v). LC-MS: m/z 1089 [M+H]$^{1+}$.

The fmoc protected intermediate (0.15 g, 0.14 mmol) was dissolved in THF (5 mL) and Et$_2$NH (2 mL) was added. The mixture was allowed to stir for 45 minutes at 45° C. The solution was concentrated under reduced pressure and concentrated in toluene. ESI-MS: m/z 857 [M+H]$^{1+}$. The $N^\epsilon$-deprotetced lysine derivative (0.14 mmol) was dissolved in DMF (3 mL) and was added to a solution of D-(+)-biotin (34 mg, 1 equiv.), TBTU (45 mg, 1 equiv.) and DiPEA (61 uL, 2.5 equiv.) in DMF (4 mL) that had been stirred under a nitrogen atmosphere for 1 h. The resulting mixture was stirred for 16 h.

The solvent was removed under reduced pressure. EtOAc (30 mL) was added and stirred. The solid product 3 was collected by filtration and was washed with MeOH and EtOAc and dried in vacuo. Yield 86 mg (57%). Rf 0.15 (DCM/MeOH, 9/1, v/v). ESI-MS: 1083.6 $[M+H]^+$.

General Procedure for Preparation of Compounds III and IV:

The carboxylic acid derivative (33 μmol) (i.e. compound 3 or 11) was dried by repeated concentration in dry DMF (2×2 mL), dissolved in DMF (1 mL) and stirred in the presence of TBTU (11 mg, 33 μmol) and DiPEA (5.7 μL, 33 μmol), under an atmosphere of $N_2$. After 1 h, pentasaccharide 4 (31 μmol) was added. The reaction mixture was stirred for 16 h at RT and analyzed by ion exchange (Mono-Q) chromatography. The reaction mixture was concentrated (<50° C., 15 mmHg). The (crude) product (10 mg/mL in $H_2O$/t-BuOH, 1/1, v/v) was deprotected by hydrogenation ($H_2$) over 10% Pd/C (an equal amount in weight was added with respect to the crude product). After 16 h the solution was degassed, filtered over a 0.45 μM HPLC filter and concentrated under reduced pressure (<50° C., 15 mmHg). The conjugate was purified by ion exchange chromatography (Q-sepharose, buffer: $H_2O \rightarrow 2M$ NaCl), followed by desalting with a Sephadex G25-column ($H_2O$) and lyophilization.

Methyl O-2,3-di-O-methyl-4-O-<<<12-N-<<$N^\epsilon$-(D-(+)-biotinyl)-N-<)]-{4-[[4-[[(1R)-1-[[4-(aminoimi-nomethyl)phenyl]methyl]-2-oxo-2-(1-piperidinyl) ethyl]amino]-3-[[(4-methoxy-2,3,6-trimethylphenyl) sulfonyl]amino]-1,4-(S)-dioxo-butyl]amino]-butanoyl)-L-lysyl>>-12-aza-3,6,9-trioxa-dode-cyl>>>-6-O-sulfo-alpha-D-glucopyranosyl-(1→4)-O-2,3-di-O-methyl-beta-D-glucopyranuronosyl-(1→4)-O-2,3,6-tri-O-sulfo-alpha-D-glucopyranosyl-(1→4)-O-2,3-di-O-methyl-alpha-L-idopyranuronosyl-(1→4)-3-O-methyl-2,6-di-O-sulfo-alpha-D-glucopyranoside octakis sodium salt (III)

Compound III was prepared and purified by conjugation of compound 3 (86 mg, 81 μmol) with compound 4 (0.14 g, 80 μmol), which was prepared as described in WO 01/42262, according to the general procedure. Yield 0.14 g (60%). ESI/TOF-MS: 880.91 $[M-3H]^{3-}$, 888.57 $[M-3H+Na]^{3-}$, 660.43 $[M-4H]^{4-}$.

1H-NMR ($D_2O$, 600 MHz); reference water signal at 4.71 ppm hampers reliable integration of signals between 4.80-4.50 ppm. δ 7.66 (m, 2H), 7.30 (m, 2H), 6.74 (m, 1H), 5.36 (m, 1H), 5.25 (m, 1H), 5.05 (m, 1H), 4.98 (m, 1H), 4.84 (m, 1H), 4.46 (m, 2H), 4.31 (m, 1H), 4.27-4.13 (5H), 4.13-3.99 (5H), 3.92 (m, 1H), 3.88-3.70 (8H), 3.70-3.07 (49H±5), 3.07-2.92 (4H), 2.85 (m, 1H), 2.76 (m, 1H), 2.65 (m, 1H), 2.51 (s, 3H), 2.40 (s, 3H), 2.36-2.22 (m, 2H), 2.21-2.11 (m, 2H), 2.08 (m, 1H), 2.06-1.91 (4H), 1.83-1.03 (20H±2).

Scheme 1

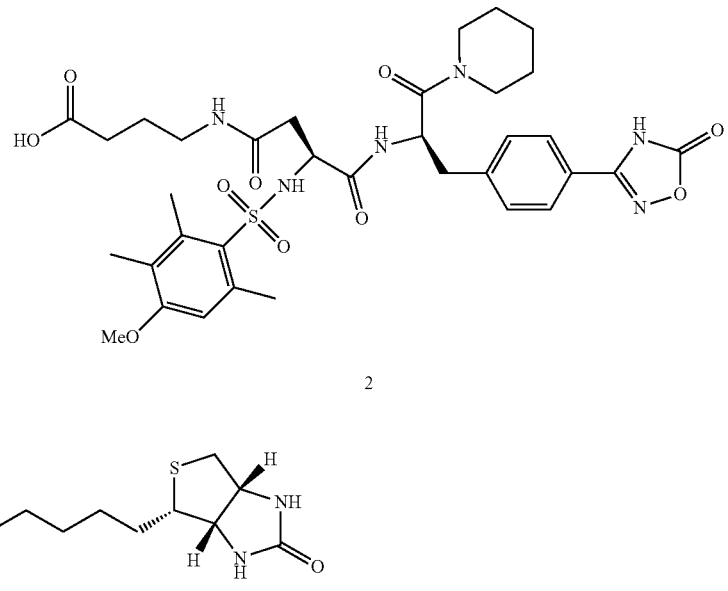

-continued
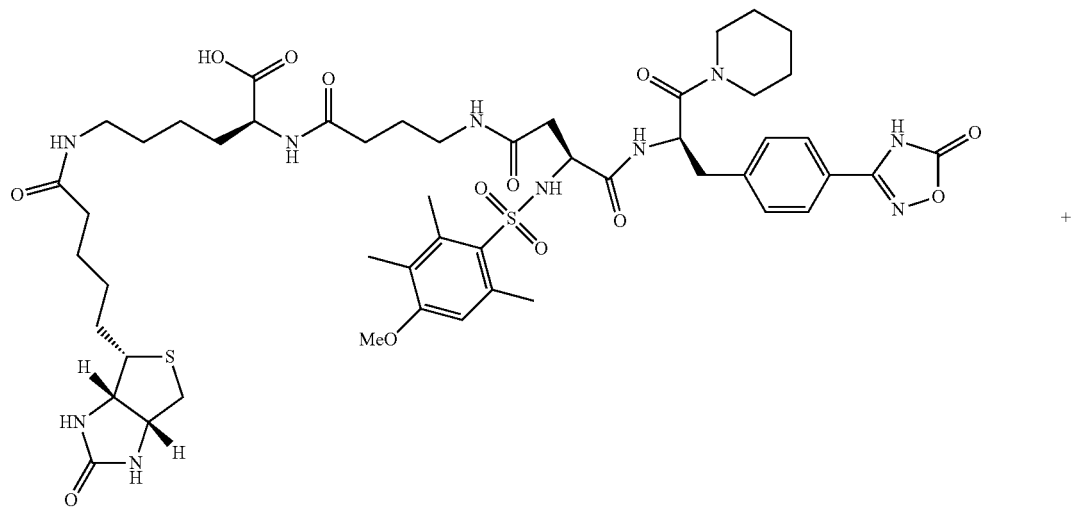
3
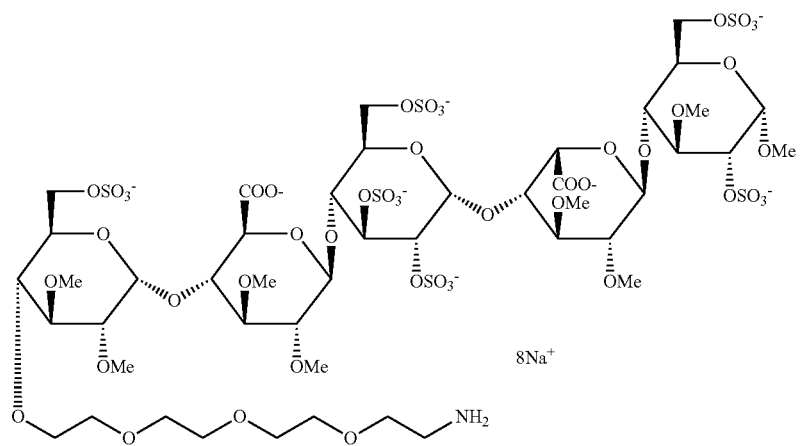
4

-continued

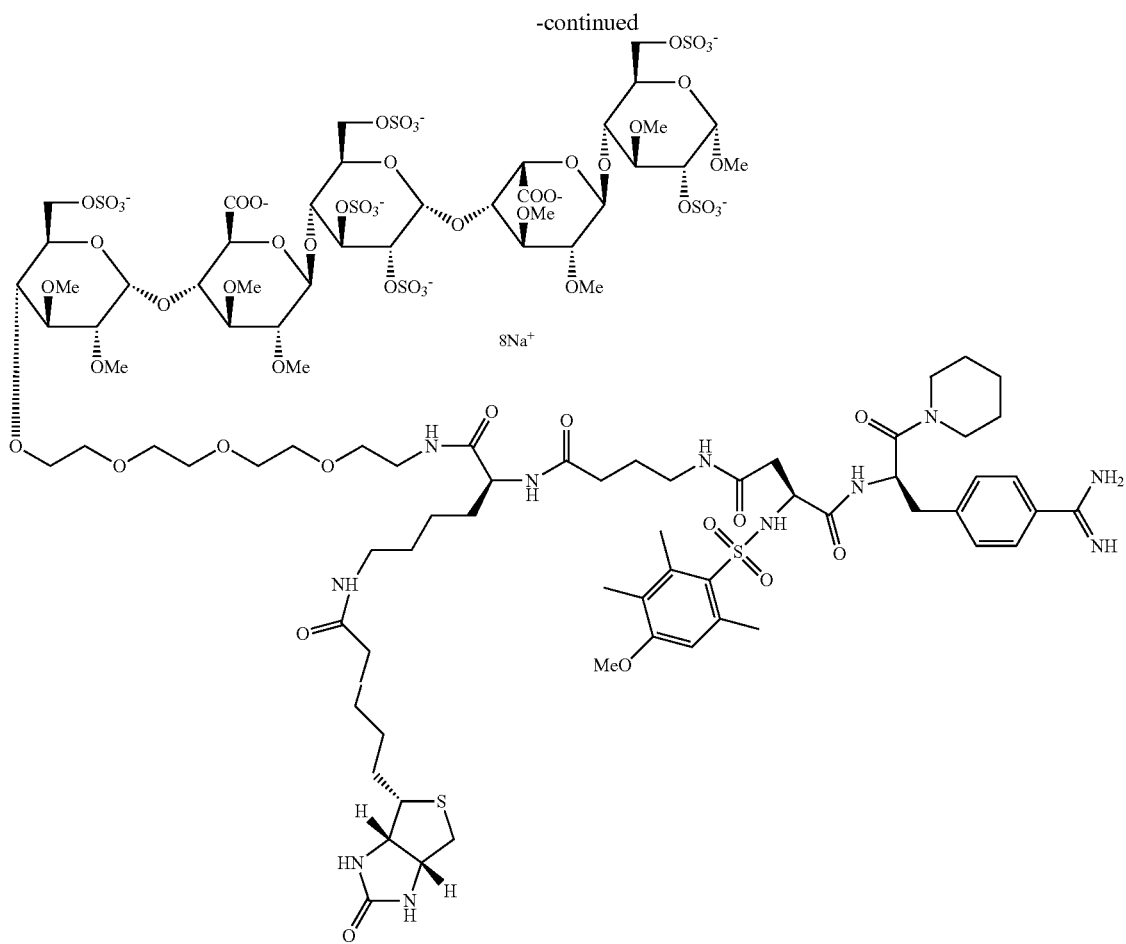

III

Example 2

Scheme 2 tert-Butyl 15-N-(9-fluorenylmethyloxycarbonyl)-15-aza-3,6,9,12-tetraoxa-pentadecanoate (6)

tert-Butyl 15-amino-3,6,9,12-tetraoxa-pentadecanoate (5) (0.50 g, 1.45 mmol) was dissolved in THF (7.5 mL) and H₂O (5 mL). 4 N NaOH solution was added until pH was approximately 9. N-9-Fluorenylmethyl carbamate-succinimide (FmocOSu, 0.54 g, 1.60 mmol, 1.1 eq) was added in portions. After 10 min. additional 4 N NaOH solution was added to adjust the pH to approximately 9. After 3 h the reaction mixture was acidified with 1 N HCl solution to pH 6-7. H₂O was added to the reaction mixture which was then extracted 3 times with EtOAc. The organic phase was washed with brine and dried over MgSO₄. After filtration the solvent was removed under reduced pressure (50 mbar, 50° C.). The crude oil was purified by silica column chromatography (DCM/MeOH, 1/0→95/5, v/v), to give compound 6 as a yellowish oil (0.61 g, 79%). Rf 0.64 (DCM/MeOH, 95/5, v/v).

15-N-(9-Fluorenylmethyloxycarbonyl)-15-aza-3,6,9,12-tetraoxa-pentadecanoate (7)

Compound 6 was dissolved in DCM (3.5 mL) and TFA (3.5 mL) was added under a nitrogen atmosphere. After 1.5 h of stirring the reaction mixture was concentrated under reduced pressure. Then the excess of TFA was removed by repeated concentration in toluene. DCM/Et₂O (100 mL, 1/2, v/v) was added and washed with 1 N HCl. The water layer was extracted with DCM/Et₂O (100 mL, 1/2, v/v). The combined organic layers were washed with brine and dried over MgSO₄. After filtration the solvent was removed under atmospheric pressure (50° C.). The crude oil was purified by silica column chromatography (DCM/MeOH/AcOH, 99/0/1→89/10/1, v/v/v), to give compound 7. Remaining AcOH was removed by dissolving the crude oily product in DCM/Et₂O (1/2, v/v) and washing with H₂O (3 times) and brine followed by drying over MgSO₄. After filtration the solvent was removed under atmospheric pressure (50° C.) to give compound 7 as a yellowish oil (0.37 g, 67%). Rf 0.32 (DCM/MeOH, 89/10/1, v/v).

tert-Butyl 15-N-(9-Fluorenylmethyloxycarbonyl)-15-aza-3,6,9,12-tetraoxa-pentadecanoyl-ε-N-(Z)-L-lysine (8)

Compound 7 (0.37 mg, 0.77 mmol) was dissolved in DCM (18 mL). DIPEA (0.40 μL, 2.31 mmol, 3 eq) and TBTU (0.25 g, 0.77 mmol) were subsequently added under an atmosphere of N₂ and the solution was allowed to stir for 10 min. Then ε-(Z)-L-Lys-OtBu.HCl (0.29 g, 0.77 mmol) was added and the mixture was stirred for an additional 1.5 h. The reaction mixture was diluted with DCM and rinsed with H₂O, 0.1 N HCl, sat. NaHCO$_3$-sol. and brine. The organic phase was dried (MgSO$_4$) and concentrated under atmospheric pressure. Purification was effected by silica gel column chromatography (DCM/MeOH, 1/0→9/1, v/v), to give compound 8 as a yellowish oil (0.51 g, 83%). Rf 0.85 (DCM/MeOH, 9/1, v/v). ESI-MS: 792.6 [M+H]$^+$, 814.6 [M+Na]$^+$, 736.4 [M−tBu+H]$^+$ tert-Butyl 15-N-tert-butyloxycarbonyl-15-aza-3,6,9,12-tetraoxa-pentadecanoyl-ϵ-N-(Z)-L-lysine (9)

Compound 8 (0.26 g, 0.32 mmol) was dissolved in THF (5 mL). Et$_2$N (1 mL) was added and the solution was allowed to stir for 24 h. The excess Et$_2$N and solvent were removed under reduced pressure (50° C.). Toluene was added and removed under reduced pressure (50° C., 65 mbar) to give the N-deprotected intermediate product (0.21 g, 0.32 mmol), Rf 0.23 (DCM/MeOH, 9/1, v/v) ESI-MS: 570.4 [M+H]$^+$, 514.4 [M−tBu+H]$^+$. The crude product was dissolved in DCM (3 mL). Et$_3$N (0.11 mL) was added followed by di-tert-butyl dicarbonate (73 mg, 0.34 mmol, 1.1 eq) under an atmosphere of N$_2$. After stirring for 5 h the mixture was added to a cold (5° C.) solution of 0.1 N HCl and extracted with EtOAc. The organic layer was washed with brine and dried (MgSO$_4$). After filtration the solvents were removed under reduced pressure (180 mbar, 50° C.). Purification was effected by silica gel column chromatography (DCM/MeOH, 1/0→95/5, v/v), to give 9 as a colorless oil (0.17 g, 82%). Rf 0.5 (DCM/MeOH, 9/1, v/v). ESI-MS: 670.6 [M+H]$^+$, 692.4 [M+Na]$^+$, 570.4 [M−Boc+H]$^+$, 514.1 [M−Boc−tBu+H]$^+$.

15-aza-3,6,9,12-tetraoxa-pentadecanoyl-ϵ-[D-(+)-biotinyl]-L-lysine (10)

Compound 9 (0.23 g, 0.34 mmol) was dissolved in EtOH (8 mL) and H$_2$O (1.2 mL). After flushing the solution with nitrogen for 5 minutes, Pd/C 10% (0.11 g) was added. Hydrogen was passed trough the solution for 4 h. Nitrogen was flushed trough the solution for 10 minutes to remove all hydrogen. The mixture was filtered over decalite and was concentrated under reduced pressure (170 mbar, 50° C.) to give the N-L-lysine deprotected intermediate as a colorless oil (0.15 g, 81%). Rf 0.02 (DCM/EtOAc, 9/1, v/v).

D-(+)-Biotine (75 mg, 0.31 mmol) was suspended in DCM (7 mL). DIPEA (0.11 mL, 0.62 mmol, 2 eq) and TBTU (0.10 g, 0.31 mmol) were subsequently added under an atmosphere of N$_2$ and the solution was allowed to stir for 1 h. A solution of the above described N-L-lysine deprotected intermediate in DCM (3 mL) was added to the reaction mixture. The mixture was allowed to stir for 16 h. H$_2$O was added and extracted with DCM (3×). The organic layer was dried (MgSO$_4$), filtered and concentrated under reduced pressure (850 mbar, 50° C.). Purification was effected by silica gel column chromatography (eluens: DCM/MeOH, 1/0→9/1 v/v), to give an oil (0.13 g, 60%). Rf 0.48 (DCM/MeOH, 9/1, v/v). ESI-MS: 762.6 [M+H], 784.6 [M+Na], 662.4 [M−Boc+H], 606.4 [M−Boc−tBu+H]. The oil was dissolved in a dry 4 N HCl solution in dioxane (4 mL) and stirred. After 1 h an insoluble oil appeared after which the solvent was removed under reduced pressure (100 mbar, 50° C.) to give compound 10 in quantitative yield. ESI-MS: 606.4 [M+H]$^+$, 628.4 [M+Na]$^+$.

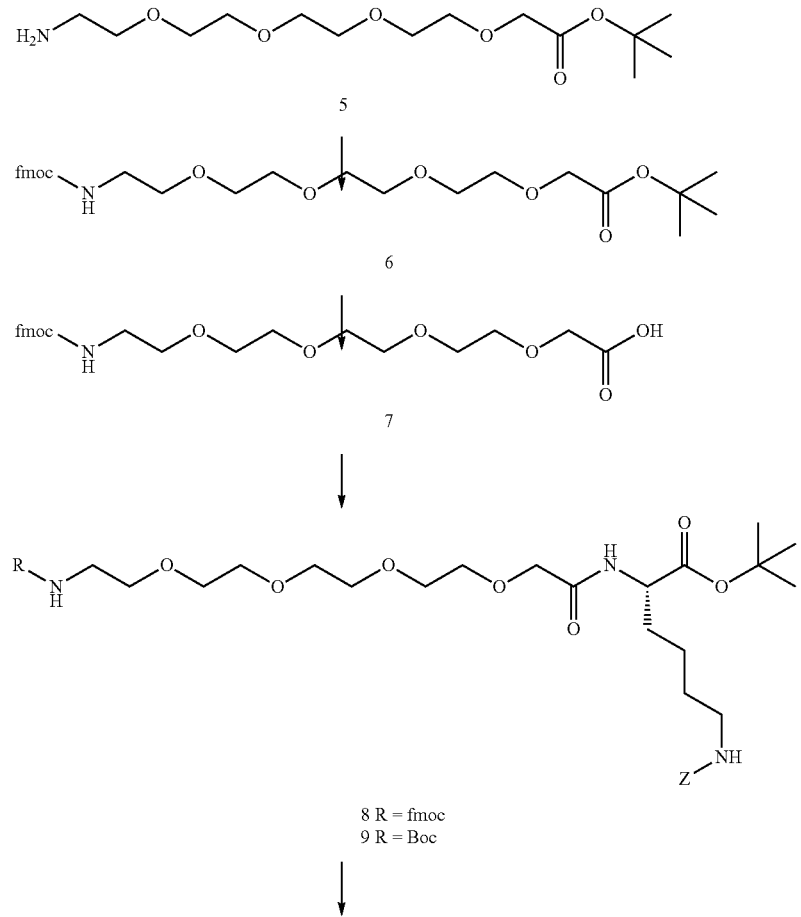

Scheme 2

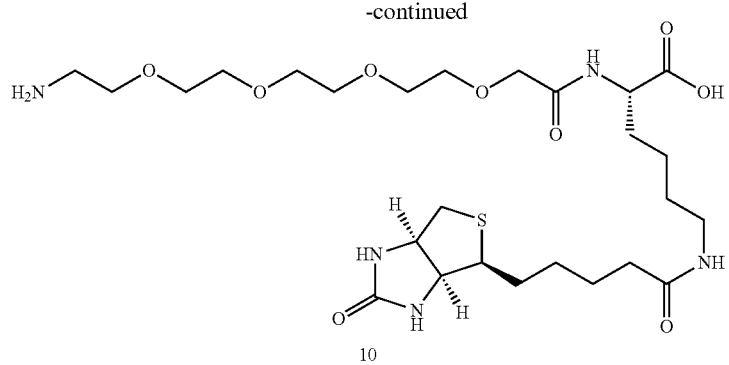

Scheme 3

N$^\epsilon$-(D-(+)-biotinyl)-N-{{4-[[4-[[(1R)-1-[[4-(1,2,4-oxadiazol-5-onyl)phenyl]methyl]-2-oxo-2-(1-piperidinyl)ethyl]amino]-3-[[(4-methoxy-2,3,6-trimethylphenyl)sulfonyl]amino]-1,4-(S)-dioxo-butyl]amino]butanoyl}-15-N-(15-aza-1-oxo-3,6,9,12-tetraoxa-pentadecyl)]}-L-lysine (11)

Compound 10 (0.12 g, 0.21 mmol) was coupled to compound 2 (0.15 g, 0.21 mmol) as described for the preparation of compound 3. The crude product was purified by preparative HPLC (C18, ACN/H$_2$O, 0.01% TFA) to give compound 11 in pure form. Yield 60 mg (22%). ESI-MS: 1316.8 [M+H]$^+$ Methyl O-2,3-di-O-methyl-4-O-<<<12-N-<<N$^\epsilon$-(D-(+)-biotinyl)-N-<[15-N-(15-aza-1-oxo-3,6,9,12-tetraoxa-pentadecyl)]-{4-[[4-[[(1R)-1-[[4-(aminoiminomethyl)phenyl]methyl]-2-oxo-2-(1-piperidinyl)ethyl]amino]-3-[[(4-methoxy-2,3,6-trimethylphenyl)sulfonyl]amino]-1,4-(S)-dioxo-butyl]amino]-butanoyl}>-L-lysyl>>-12-aza-3,6,9-trioxa-dodecyl>>>-6-O-sulfo-alpha-D-glucopyranosyl-(1→4)-O-2,3-di-O-methyl-beta-D-glucopyranuronosyl-(1→4)-O-2,3,6-tri-O-sulfo-alpha-D-glucopyranosyl-(1→4)-O-2,3-di-O-m ethyl-alpha-L-idopyranuronosyl-(1→4)-3-O-methyl-2,6-di-O-sulfo-alpha-D-glucopyranoside octakis sodium salt (IV)

Compound 11 was coupled to compound 4 and the intermediate conjugate was deprotected according to the general procedure to give compound IV.

Yield 9.2 mg (7.6%)

1H-NMR (D20, 600 MHz), reference water signal at 4.70 ppm hampers reliable integration of signals between 4.80-4.54 ppm. δ 7.59 (d, 2H), 7.23 (d, 2H), 6.68 (s, 1H), 5.32 (m, 1H), 5.19 (m, 1H), 4.91 (m, 1H), 4.85 (m, 1H), 4.76 (m), 4.53-4.31 (3H), 4.30-4.05 (9H), 4.04-3.90 (7H), 3.89-3.62. (7H), 3.61-3.42 (42H±4), 3.42-3.31 (18H±2), 3.31-3.14 (12H), 3.14-3.05 (5H), 3.03-2.94 (3H), 2.93-2.84 (2H), 2.81 (dd, 1H), 2.70 (dd, 1H), 2.59 (d, 1H), 2.44 (s, 3H), 2.34 (s, 3H), 2.22-2.08 (4H), 2.06 (t, 2H), 1.96 (s, 3H), 1.72-1.01 (18H±2) ESI/TOF-MS: m/z 574.72 [M−5H]$^{5-}$, at m/z 718.66 [M−4H]$^{4-}$, at m/z 958.56 [M−3H]$^{3-}$.

Scheme 3

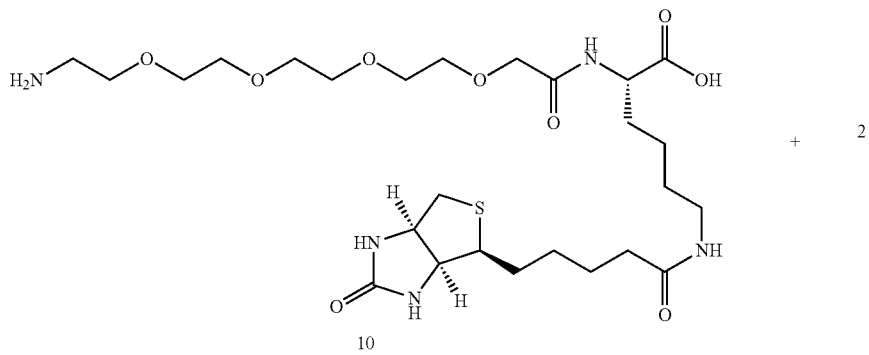

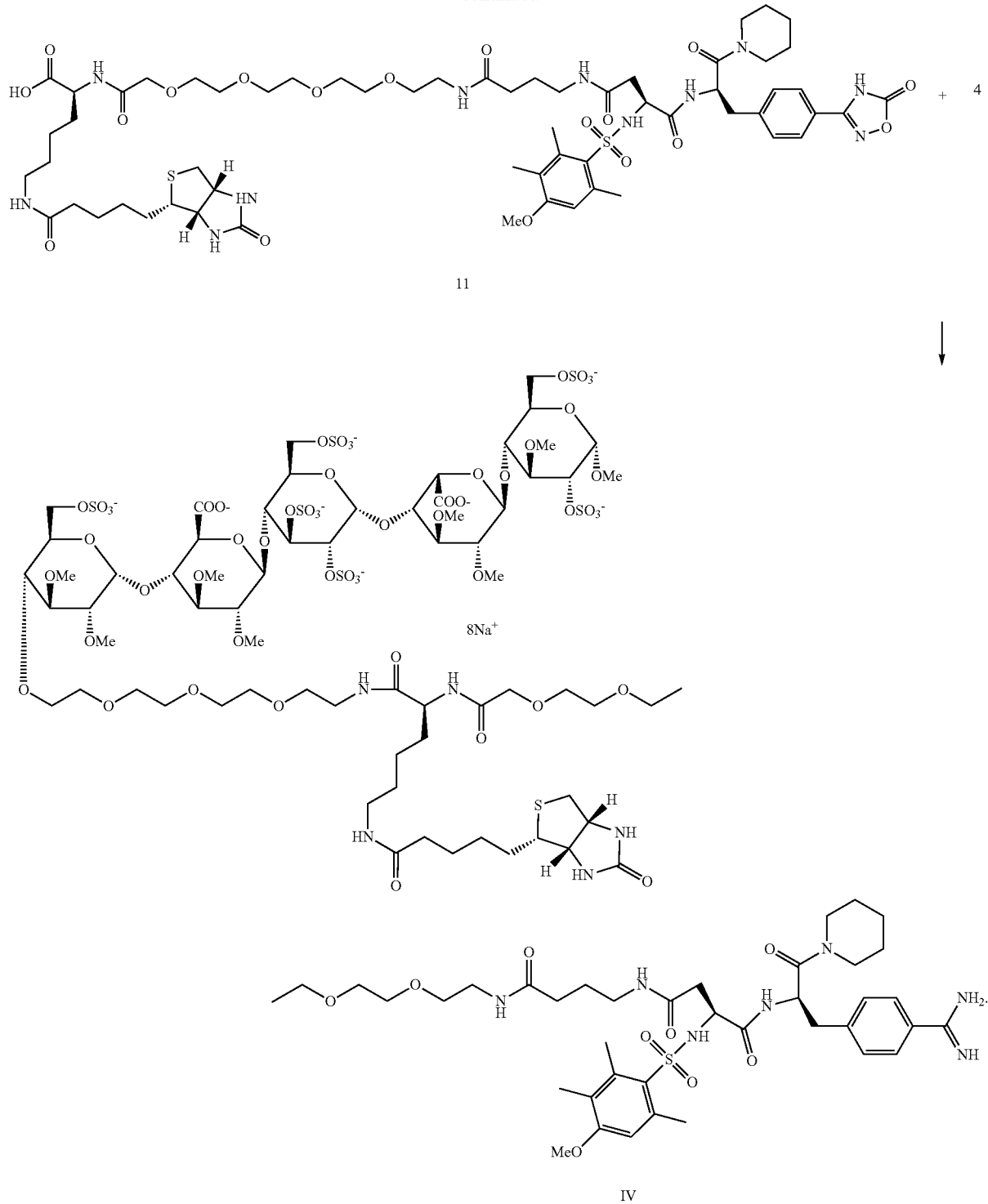

Example 3

Pharmacology

In Vitro Test for Determination of the Anti-Factor Xa and Factor IIa Activity in Human Plasma The anti-factor Xa and IIa activity of the tested compounds in human plasma were measured amidolytically using S2222 or S2238 (Chromogenix, Chromogenics Ltd, Molndal, Sweden) as substrates, respectively. The protcols were based on the method described by Teien and Lie. (Teien A N, Lie M. Evaluation of an amidolytic heparin assay method increased sensitivity by adding purified antithrombin III. Thromb. Res. 1977, 10: 399-410). Both activities are expressed in IC-50 (Mol/L).

TABLE 1

Summary of in vitro antithrombotic activities

| Compound | ORG 42675 | Compound III of this invention |
|---|---|---|
| Anti-IIa Human plasma pH 7.4 IC-50 (M) | 1.78E−08 | 1.62E−08 |
| Anti-Xa Human plasma pH 7.4 IC-50 (M) | 7.67E−10 | 8.43E−10 |

3.1 Pharmacokinetics

The pharmacokinetic properties of Org 42675 and of compound III of this invention were studied in male Wistar rats of 300-400 gr. The rats were anaesthetized by inhalation of a mixture of $O_2/N_2O$/isoflurane, after which the right jugular vein was cannulated. The next day rats were treated s.c. with doses of 100 nmol/kg. After s.c. administration, blood was sampled at several time intervals. Then the blood was centrifuged after which the plasma was siphoned off and stored at −20° C. until use. The concentration of the tested compound was measured amidolytically using S-2222 or S-2238 as substrates (Chromogenix, Chromogenics Ltd, Molndal, Sweden) to determine the anti-Xa or anti-IIa activity, respectively. Both procedures were based on the methods of Teien and Lie (Teien A N, Lie M. Evaluation of an amidolytic heparin assay method increased sensitivity by adding purified antithrombin III. Thromb. Res. 1977, 10: 399-410). The concentrations in the obtained plasma samples were determined against a calibration curve which was made of the stock solution of the tested compound itself. The concentration in the samples was expressed in nmol/mL and the kinetic parameters were calculated with the noncompartment model of WinNonlin. (see FIG. 1)

TABLE 2

Pharmacokinetic parameters after s.c. administration of compound III of this invention or Org 42675 (100 nmol/kg) in rat. Experiment performed in n = 3/treatment.

| | Compound III of this invention Mean ± s.e.m. anti_Xa | Compound III of this invention Mean ± s.e.m. anti-IIa | Org 42675 Mean ± s.e.m. anti_Xa |
|---|---|---|---|
| Tmax (h) | 1.2 ± 0.4 | 1.5 ± 0.5 | 2.3 ± 0.2 |
| Cmax (nmol/mL) | 1.1 ± 0.1 | 1.1 ± 0.3 | 1.0 ± 0.02 |
| T1/2 eli (h) | 3.9 ± 0.3 | 2.7 ± 0.5 | 2.7 ± 0.2 |
| AUCinf (h · nmol/mL) | 7.2 ± 0.2 | 5.0 ± 0.6 | 5.3 ± 0.3 |
| Vz (mL/kg) | 78 ± 4.6 | 78 ± 4.2 | 74 ± 4.5 |
| Cl (mL/h/kg) | 13.9 ± 0.4 | 20.6 ± 2.4 | 19.1 ± 1.1 |
| MRT (h) | 5.9 ± 0.5 | 4.3 ± 0.3 | 4.6 ± 0.2 |

It is concluded that within the variability of the experiment compound III of this invention and Org 42675 show the same pharmacokinetic behavior in rats.

3.2 Pharmacokinetics—Neutralization Experiment:

Rats were treated with compound III of this invention, or Org 42675 at a dose of 100 nmol/kg s.c. At t=2 h, a blood sample was taken and 10 mg/kg of Avidin (from egg white, Sigma) was administered i.v. to the rats treated with compound III of this invention or Org 42675. Blood was sampled at 0.17, 0.5, 1, 2, 3, and 7 hours subsequently. The blood was treated as described in the pharmacokinetic experiment and the concentration of the samples was determined by measuring the (residual) anti-Xa or anti-IIa activity. (see FIG. 2)

TABLE 3

The area under the curves (AUC's) calculated after s.c. administration of 100 nmol/kg of compound III of this invention or Org 42675 and avidin (10 mg/kg) at t = 2 h. Data calculated from T = 2 h. Experiment performed in n = 3/treatment.

| | Compound III of this invention Mean ± s.e.m. anti_Xa | Compound III of this invention Mean ± s.e.m. anti-IIa | Compound Org 42675 Mean ± s.e.m. anti_Xa |
|---|---|---|---|
| AUCinf (h · nmol/mL) | 1.2 ± 0.1 | 0.8 ± 0.1 | 4.8 ± 0.6 |

It is concluded that after s.c. administration of compound III of this invention (100 nmol/kg), the antithrombotic activity as determined by measuring the (residual) anti-Xa and anti-IIa activity can be neutralized by administration of 10 mg/kg i.v. of avidin. The neutralization of compound III of this invention by avidin is reflected by the is reflected by the rapid reduction of its plasma concentration and the strongly reduced AUCinf. of compound III of this invention after administration of Avidin in comparison to compound Org 42675. Furthermore, the pharmacokinetic behavior of the non-biotinylated equivalent compound Org 42675 is not affected by the addition of avidin. The latter confirms that the neutralization is associated with the presence of the biotin label and that it does not affect the pharmacokinetic behavior of the dual inhibitor.

The invention claimed is:

1. A method for treating thrombosis in a subject in need of such treatment, the method comprising administering to the subject an effective amount of an antithrombotic compound of the formula (I)

oligosaccharide-spacer-A    (I), wherein the oligosaccharide is a negatively charged pentasaccharide of the formula (II)

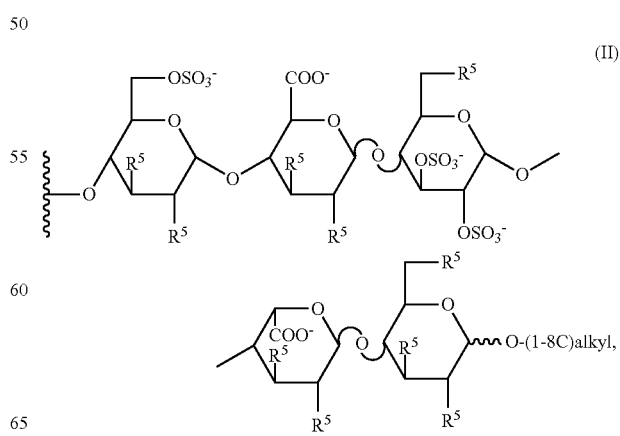

wherein R⁵ is OSO₃⁻ or (1-8C)alkoxy, the charge being compensated by positively charged couriterions;
the spacer is a)

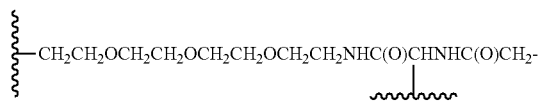

b)

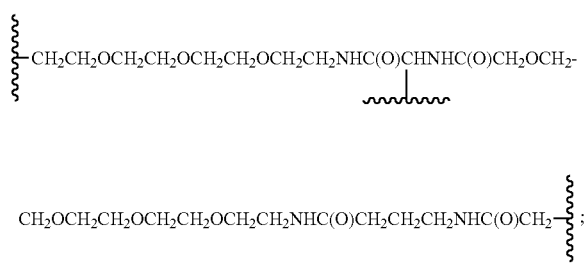

A is the residue —CH[NH—SO₂—R¹][CO—NR²—CH(4-benzamidine)-CO—NR³R⁴],
wherein R¹ is phenyl, naphthyl, 1,2,3,4-tetrahydronaphthyl, (iso)quinolinyl, tetrahydro(iso)quinolinyl, 3,4-dihydro-1H-isoquinolinyl, chromanyl or the camphor group, which groups may optionally be substituted with one or more substituents selected from (1-8C)alkyl or (1-8C)alkoxy; and wherein R² and R³ are independently H or (1-8C)alkyl; R⁴ is (1-8C)alkyl or (3-8C)cycloalkyl; or R³ and R⁴ together with the nitrogen atom to which they are bonded are a nonaromatic (4-8) membered ring optionally containing another heteroatom, the ring optionally being substituted with (1-8C)alkyl or SO₂-(1-8C)alkyl;
or a pharmaceutically acceptable salt thereof;
wherein the spacer of the compound of formula I comprises at least one covalent bond with a biotin residue or an analogue of the formula —(CH₂)₄—NR-BT, where BT is the residue

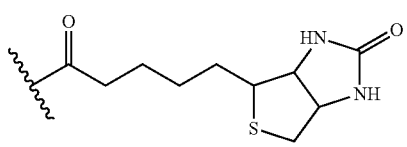

where R is H or (1-4C)alkyl,
and neutralizing the anti-thrombotic ac of the compound by administering avidin or streptavidin.

2. The method of claim 1, wherein the pentasaccharide residue has the structure

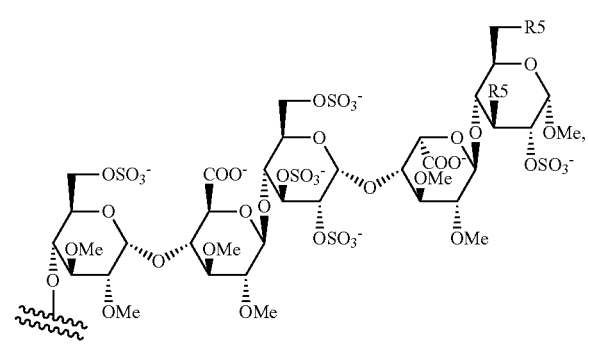

wherein R⁵ is OCH₃ or OSO₃⁻.

3. The method of claim 2, wherein the pentasaccharide residue has the structure

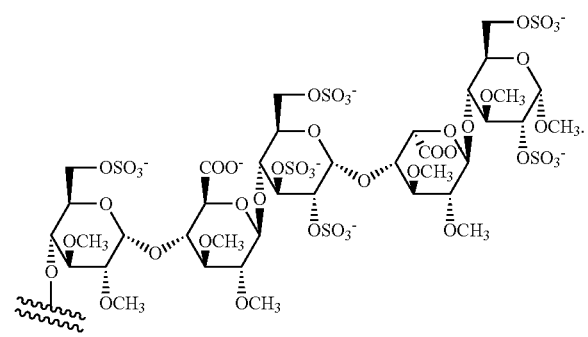

4. The method of claim 1, wherein R¹ is phenyl or naphthyl, optionally substituted with one or more substituents selected from methyl or methoxy.

5. The method of claim 4, wherein R¹ is 4-methoxy-2,3,6-trimethylphenyl.

6. The method of claim 1, wherein NR³R⁴ represents the piperidinyl group.

7. The method of claim 1, wherein R² is H.

8. The method of claim 1, where the compound is
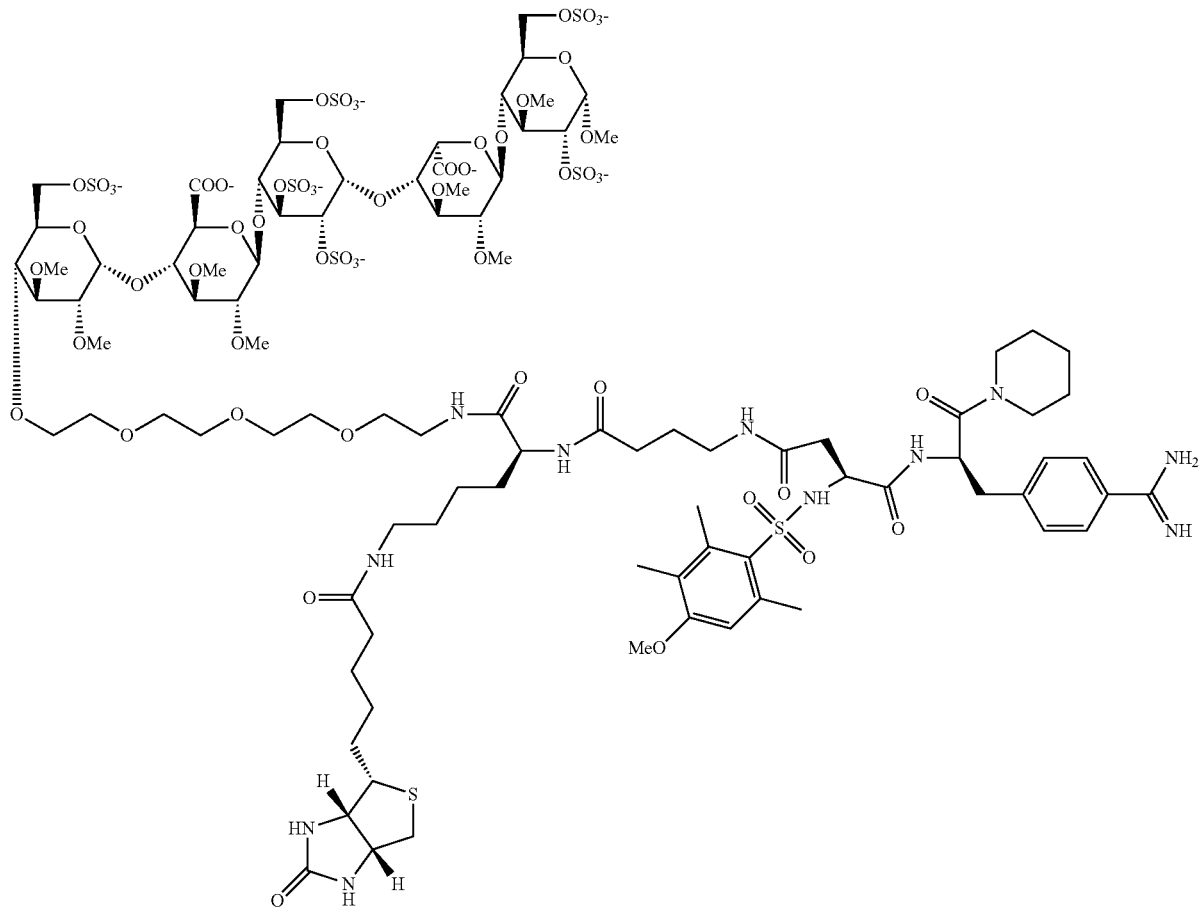
or a pharmaceutically acceptable salt thereof.
9. The method of claim 8, where the compound is in the form of a sodium salt.
* * * * *